(12) United States Patent
Tadenuma et al.

(10) Patent No.: US 9,797,003 B2
(45) Date of Patent: Oct. 24, 2017

(54) NUCLEIC ACID SEQUENCE MEASURING METHOD, NUCLEIC ACID SEQUENCE MEASURING DEVICE, MANUFACTURING METHOD FOR NUCLEIC ACID SEQUENCE MEASURING DEVICE, AND NUCLEIC ACID SEQUENCE MEASURING APPARATUS

(71) Applicant: YOKOGAWA ELECTRIC CORPORATION, Musashino-shi, Tokyo (JP)

(72) Inventors: Takashi Tadenuma, Musashino (JP); Tomoyuki Taguchi, Musashino (JP); Takeo Tanaami, Musashino (JP)

(73) Assignee: YOKOGAWA ELECTRIC CORPORATION, Tokyo (JP)

(*) Notice: Subject to any disclaimer, the term of this patent is extended or adjusted under 35 U.S.C. 154(b) by 251 days.

(21) Appl. No.: 14/469,563

(22) Filed: Aug. 26, 2014

(65) Prior Publication Data
US 2015/0065377 A1 Mar. 5, 2015

(30) Foreign Application Priority Data
Aug. 27, 2013 (JP) ................................. 2013-175500

(51) Int. Cl.
*C12Q 1/68* (2006.01)
*C07H 21/00* (2006.01)

(52) U.S. Cl.
CPC ......... *C12Q 1/6818* (2013.01); *C12Q 1/6834* (2013.01); *Y10T 436/143333* (2015.01)

(58) Field of Classification Search
CPC ......... C12C 1/68; C12M 1/00; C12M 1/3476; C07H 21/00
See application file for complete search history.

(56) References Cited

U.S. PATENT DOCUMENTS

| | | | | |
|---|---|---|---|---|
| 4,766,062 A * | 8/1988 | Diamond | .............. | C12Q 1/6813 435/6.1 |
| 5,556,751 A * | 9/1996 | Stefano | ................ | C12Q 1/6867 435/6.11 |
| 5,780,233 A * | 7/1998 | Guo | ..................... | C12Q 1/6827 435/6.1 |
| 6,815,163 B1 * | 11/2004 | Breslauer | ............. | C12Q 1/6818 435/6.1 |
| 7,381,818 B2 * | 6/2008 | Lokhov | ................... | C07H 21/04 435/91.2 |
| 2002/0064772 A1 | 5/2002 | Gildea et al. | | |
| 2002/0106653 A1 | 8/2002 | Kurane et al. | | |
| 2003/0129611 A1 * | 7/2003 | Bao | ...................... | C12Q 1/6818 435/6.11 |
| 2004/0009514 A1 * | 1/2004 | Frutos | .................... | C07H 21/00 506/9 |
| 2004/0023216 A1 * | 2/2004 | Lu | ............................ | C12Q 1/68 435/6.11 |
| 2005/0045846 A1 * | 3/2005 | Iwabuchi | ................ | F16K 51/02 251/193 |
| 2007/0059693 A1 | 3/2007 | Miller et al. | | |
| 2007/0072199 A1 * | 3/2007 | Levicky | ................. | B01J 20/289 435/6.12 |
| 2012/0052494 A1 * | 3/2012 | Li | .......................... | C12Q 1/689 435/6.11 |
| 2012/0237451 A1 * | 9/2012 | Chen | .................... | C12Q 1/6818 424/9.6 |
| 2012/0295805 A1 * | 11/2012 | Levicky | ............. | G01N 21/6428 506/9 |
| 2014/0011189 A1 | 1/2014 | Miller et al. | | |
| 2015/0141285 A1 * | 5/2015 | Levicky | ............... | C12Q 1/6816 506/9 |

FOREIGN PATENT DOCUMENTS

| | | |
|---|---|---|
| CN | 1434286 A | 8/2003 |
| CN | 102154276 A | 8/2011 |
| JP | 2003-526597 A | 9/2003 |
| JP | 2004-248678 A | 9/2004 |
| WO | 99/21881 A1 | 5/1999 |
| WO | 2004/061127 A2 | 7/2004 |

OTHER PUBLICATIONS

Brown et al., Chem. Comm. 2000 : 621.*
Du et al., JACS 127 : 7932 (2005).*
Morrison et al., Solution-phase detection of polynucleotides using interacting fluorescent labels and competitive hybridization. Analytical Biochemistry 1283 : 231 (1989).*
Morrison et al., Biochemistry 32 : 3095 (1993).*
Stemmers et al., Screening unlabeled DNA targets with randomly ordered fiber-optic gene arrays. Nature Biotechnology 18 : 91 (2000).*
Tsourkas et al., Nucleic Acids Research 30 (19) : 4208 (2002).*
Yao et al., Analytical Biochemistry 331 : 216 (2004).*
Fang et al.,Designing a Novel Molecular Beacon for Surface-Immobilized DNA Hybridization Studies. JACS 121 : 2921 (1999).*
Guo et al., Enhanced discrimination of single nucleotide polymorphisms by artificial mismatch hybridization. Nature Biotechnology 15 : 331 (1997).*
Li et al.,A new class of homogeneous nucleic acid probes based on specific displacement hybridization. Nucleic Acids Research 30 (2) : e5 (2002).*
Morrison et al., Solution-phase detection of polynucleotides using interacting fluorescent labels and competitive hybridization. Analytical Biochemistry 183(2) : 231 (1989).*

(Continued)

*Primary Examiner* — Ethan C Whisenant
(74) *Attorney, Agent, or Firm* — Hauptman Ham, LLP

(57) ABSTRACT

A nucleic acid sequence measuring method includes measuring fluorescence from the nucleic acid sequence measuring device supplied with a sample solution. The device includes a fluorescent probe added with a fluorescent molecule, and a quenching probe added with a quenching substance. The fluorescent probe and/or the quenching probe has a detection part detecting a predetermined nucleic acid sequence. Fluorescence from the fluorescent molecule is quenched by the quenching substance coupled with the fluorescent molecule when the hybridization between the detection target nucleic acid and the detection part has not occurred, and fluorescence is emitted from the fluorescent molecule separated from the quenching substance when the hybridization has occurred.

16 Claims, 11 Drawing Sheets

(56) References Cited

OTHER PUBLICATIONS

Xiaohong Fang et al., "Designing a Novel Molecular Beacon for Surface-Immobilized DNA Hybridization Studies", J. Am. Chem. Soc., 1999, vol. 121, pp. 2921-2922.
Shuichi Kaneko, et al., "Handbook of Biochip Technology", Apr. 8, 2010, p. 604, NTS Inc., Tokyo Japan.

* cited by examiner

NUCLEIC ACID SEQUENCE MEASURING METHOD, NUCLEIC ACID SEQUENCE MEASURING DEVICE, MANUFACTURING METHOD FOR NUCLEIC ACID SEQUENCE MEASURING DEVICE, AND NUCLEIC ACID SEQUENCE MEASURING APPARATUS

CROSS-REFERENCE TO RELATED APPLICATION

This application claims priority from Japanese Patent Application No. 2013-175500 filed with the Japan Patent Office on Aug. 27, 2013, the entire content of which is hereby incorporated by reference.

BACKGROUND

1. Technical Field

The present disclosure relates to a nucleic acid sequence measuring method, a nucleic acid sequence measuring device, a manufacturing method for nucleic acid sequence measuring device, and a nucleic acid sequence measuring apparatus.

2. Background Art

A nucleic acid sequence measuring method has been known in which a target having a particular nucleic acid sequence in a sample is measured through hybridization between the target and a probe by using a nucleic acid sequence measuring device. For example, a method of checking the presence or absence of, or measuring the amount of a predetermined nucleic acid by using a DNA chip as a nucleic acid sequence measuring device has been widely known. The DNA chip includes a detection probe with a sequence complementary with the nucleic acid to be detected, the detection probe being fixed to the solid surface of a substrate or the like. The detection probe is fixed to the solid surface at any of 3' end and 5' end thereof. On the other hand, the nucleic acid to be detected (target) is modified with a fluorescent molecule or the like.

For example, the measurement using the DNA chip is conducted based on procedures as below.

(1) The detection target nucleic acid molecule in the sample is amplified by a nucleic acid amplifying technique such as PCR. Moreover, a fluorescent molecule is added to the amplified molecule (i.e., the nucleic acid to be detected, or target). The fluorescent molecule is added in a manner that, for example, the nucleic acid with the fluorescent pigment added thereto is mixed in the PCR amplification or a primer to which the fluorescent pigment is added in advance is used in the PCR amplification. Alternatively, the fluorescent pigment is added by chemical modification after the amplification.

(2) A solution containing the target is prepared and added to the DNA chip having the detection probe. The target modified with the fluorescence is captured by the detection probe through the hybridization with the detection probe.

(3) By washing the DNA chip, the fluorescence emitted from the molecules that are not captured or the molecules that are coupled nonspecifically to the nucleic acid sequence of the detection probe is eliminated. This washing step is repeated for a plurality of times depending on the desired degree of washing. After the DNA chip is washed and before the DNA chip is measured, the solid surface is dried up.

(4) The solid surface is observed using a fluorescence reading apparatus. The presence or absence of the target in the sample is checked based on whether the detection probe of the DNA chip exhibits the fluorescence.

SUMMARY

A nucleic acid sequence measuring method includes: preparing a sample solution containing a target nucleic acid; supplying the sample solution to a nucleic acid sequence measuring device; and measuring fluorescence from the nucleic acid sequence measuring device. The nucleic acid sequence measuring device includes: a fluorescent probe having a coupling part and a base end and added with a fluorescent molecule at a predetermined position; a quenching probe having a coupling part and a base end and added with a quenching substance at a predetermined position; and a substrate having a solid surface to which the base end of each of the fluorescent probe and the quenching probe is fixed. The coupling part of the fluorescent probe and the coupling part of the quenching probe each have a mutually complementary nucleic acid sequence; at least one of the fluorescent probe and the quenching probe has a detection part with a nucleic acid sequence complementary with a predetermined nucleic acid sequence; and the base end of the fluorescent probe and the base end of the quenching probe are fixed to the solid surface, the probes are in such a positional relationship that fluorescence from the fluorescent molecule is quenched by the quenching substance that has approached the fluorescent molecule by maintaining the coupling between the fluorescent probe and the quenching probe through the coupling parts when the hybridization between the target nucleic acid and the detection part has not occurred, and that fluorescence is emitted from the fluorescent molecule separated from the quenching substance due to canceling of the coupling between the fluorescent probe and the quenching probe through the coupling parts when the hybridization between the target nucleic acid and the detection part has occurred.

DETAILED DESCRIPTION

Figure 1:
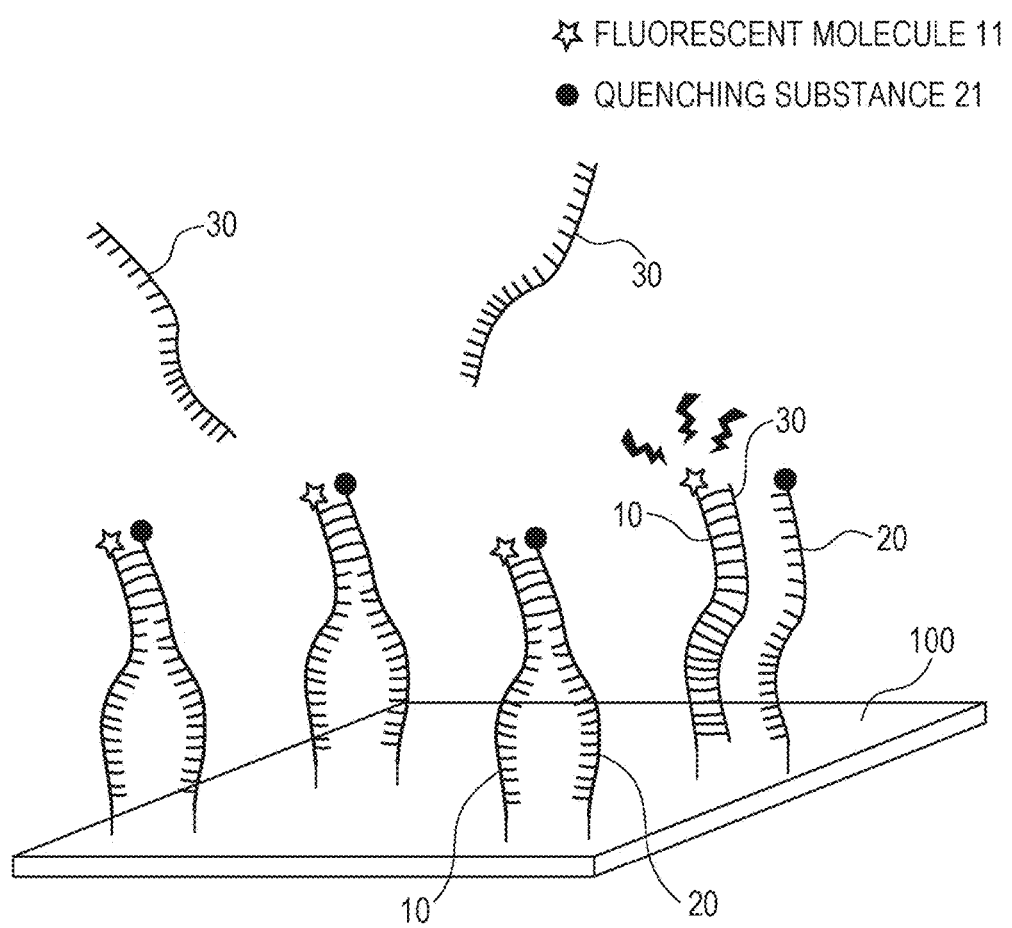
FIG. 1 is a diagram illustrating a structure of a nucleic acid sequence measuring device used in a nucleic acid sequence measuring method according to an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The aforementioned known method in which the DNA chip is used may require the step of labeling the target with the fluorescent molecule and the step of washing the DNA chip before the detection. In this case, the method becomes complicated. Depending on the way of washing the chip, the signal may deteriorate or the background noise may increase. Further, the signal within the chip plane may become uneven due to the uneven washing.

On the other hand, Handbook of Biochip Technology (Shuichi Kaneko, et. al., NTS, Page 604, issued on Apr. 6, 2010) reports the DNA chip using the molecular beacon as the detection probe. In the case of using the DNA chip with the molecular beacon, however, the quenching of the fluorescence from the fluorescent molecule becomes insufficient even in the absence of the target. Therefore, the offset fluorescence intensity increases to deteriorate the detection sensitivity of the DNA chip.

An object of the present disclosure is to provide, for example, a nucleic acid sequence measuring method with excellent detection sensitivity including a simplified nucleic acid detection step.

A nucleic acid sequence measuring method according to an embodiment of the present disclosure (the present measuring method) includes: preparing a sample solution containing a target nucleic acid; supplying the sample solution to a nucleic acid sequence measuring device; and measuring fluorescence from the nucleic acid sequence measuring device. The nucleic acid sequence measuring device includes: a fluorescent probe having a coupling part and a base end and added with a fluorescent molecule at a predetermined position; a quenching probe having a coupling part and a base end and added with a quenching substance at a predetermined position; and a substrate having a solid surface to which the base end of each of the fluorescent probe and the quenching probe is fixed. The coupling part of the fluorescent probe and the coupling part of the quenching probe each have a mutually complementary nucleic acid sequence; at least one of the fluorescent probe and the quenching probe has a detection part with a nucleic acid sequence complementary with a predetermined nucleic acid sequence; and the base end of the fluorescent probe and the base end of the quenching probe are fixed to the solid surface, the probes are in such a positional relationship that fluorescence from the fluorescent molecule is quenched by the quenching substance that has approached the fluorescent molecule by maintaining the coupling between the fluorescent probe and the quenching probe through the coupling parts when the hybridization between the target nucleic acid and the detection part has not occurred, and that fluorescence is emitted from the fluorescent molecule separated from the quenching substance due to canceling of the coupling between the fluorescent probe and the quenching probe through the coupling parts when the hybridization between the target nucleic acid and the detection part has occurred.

According to this nucleic acid sequence measuring method, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

In the present measuring method, the fluorescence from the nucleic acid sequence measuring device may be measured in the presence of the sample solution.

A nucleic acid sequence measuring device according to an embodiment of the present disclosure (the present device) configured to measure a nucleic acid sequence of a target nucleic acid in a sample solution includes: a fluorescent probe having a coupling part and a base end and added with a fluorescent molecule at a predetermined position; a quenching probe having a coupling part and a base end and added with a quenching substance at a predetermined position; and a substrate having a solid surface to which the base end of each of the fluorescent probe and the quenching probe is fixed. The coupling part of the fluorescent probe and the coupling part of the quenching probe each have a mutually complementary nucleic acid sequence; at least one of the fluorescent probe and the quenching probe has a detection part with a nucleic acid sequence complementary with a predetermined nucleic acid sequence; and the base end of the fluorescent probe and the base end of the quenching probe are fixed to the solid surface, the probes are in such a positional relationship that fluorescence from the fluorescent molecule is quenched by the quenching substance that has approached the fluorescent molecule by maintaining the coupling between the fluorescent probe and the quenching probe through the coupling parts when the hybridization between the target nucleic acid and the detection part has not occurred, and that fluorescence is emitted from the fluorescent molecule separated from the quenching substance due to canceling of the coupling between the fluorescent probe and the quenching probe through the coupling parts when the hybridization between the target nucleic acid and the detection part has occurred.

According to this nucleic acid sequence measuring device, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

In the present device, the fluorescent probe may have the detection part.

In the present device, the substrate may be a flat plate and the solid surface is one plane of the flat plate.

In the present device, the substrate may be a sphere and the solid surface is a spherical surface of the sphere.

In the present device, at least a part of the coupling part may function as the detection part.

In the present device, the number of quenching probes may be larger than that of fluorescent probes.

In the present device, the ratio between the number of fluorescent probes and the number of quenching probes may be 1:3.

In the present device, the predetermined position at which the fluorescent molecule and the quenching substance are added may be in the middle of the fluorescent probe and the quenching probe.

In the present device, there may be a plurality of predetermined positions at which the fluorescent molecule and the quenching substance are added.

In the present device, both the fluorescent probe and the quenching probe may have the detection part.

A manufacturing method for the nucleic acid sequence measuring device according to an embodiment of the present disclosure is a method for manufacturing the present device described above. That is, this manufacturing method includes: coupling the fluorescent probe and the quenching probe through the coupling parts; and coupling the fluorescent probe and the quenching probe to the solid surface with the probes coupled with each other through the coupling parts.

According to the manufacturing method for the nucleic acid sequence measuring device, the fluorescent probe and the quenching probe are coupled with the solid surface in the state that the probes are coupled with each other through the coupling parts thereof. Therefore, the positional relationship between the fluorescent probe and the quenching probe can be managed as appropriate. This enables the quenching effect to be exhibited as appropriate. Moreover, the detection sensitivity can be improved.

A nucleic acid sequence measuring apparatus according to an embodiment of the present disclosure includes the present device and a fluorescence reading apparatus configured to measure the fluorescence from the present device.

According to this nucleic acid sequence measuring apparatus, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

In the nucleic acid sequence measuring apparatus, the fluorescence from the nucleic acid sequence measuring device may be measured in the presence of the sample solution.

In the nucleic acid sequence measuring method according to an embodiment of the present disclosure, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

In the nucleic acid sequence measuring device according to an embodiment of the present disclosure, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

In the manufacturing method for the nucleic acid sequence measuring device according to an embodiment of the present disclosure, the fluorescent probe and the quenching probe are coupled with the solid surface in the state that the probes are coupled with each other through the coupling parts thereof. Therefore, the positional relationship between the fluorescent probe and the quenching probe can be managed as appropriate. This enables the quenching effect to be exhibited as appropriate. Moreover, the detection sensitivity can be improved.

In the nucleic acid sequence measuring apparatus according to an embodiment of the present disclosure, the base end of the fluorescent probe and the base end of the quenching probe, which are independent from each other, are fixed to the solid surface. This enables the quenching effect to be exhibited as appropriate. Moreover, the detection sensitivity can be improved. Furthermore, since the labeling step becomes unnecessary, the washing step can also be omitted.

Description is hereinafter made of an example of a nucleic acid sequence measuring method according to an embodiment of the present disclosure. In the description below, the nucleic acid is described as the DNA. It is needless to say that, however, the description applies to the case in which the nucleic acid is RNA. Therefore, the nucleic acid sequence measuring device functions as the DNA chip when the nucleic acid is DNA and as a RNA chip when the nucleic acid is RNA.

Figure 2:
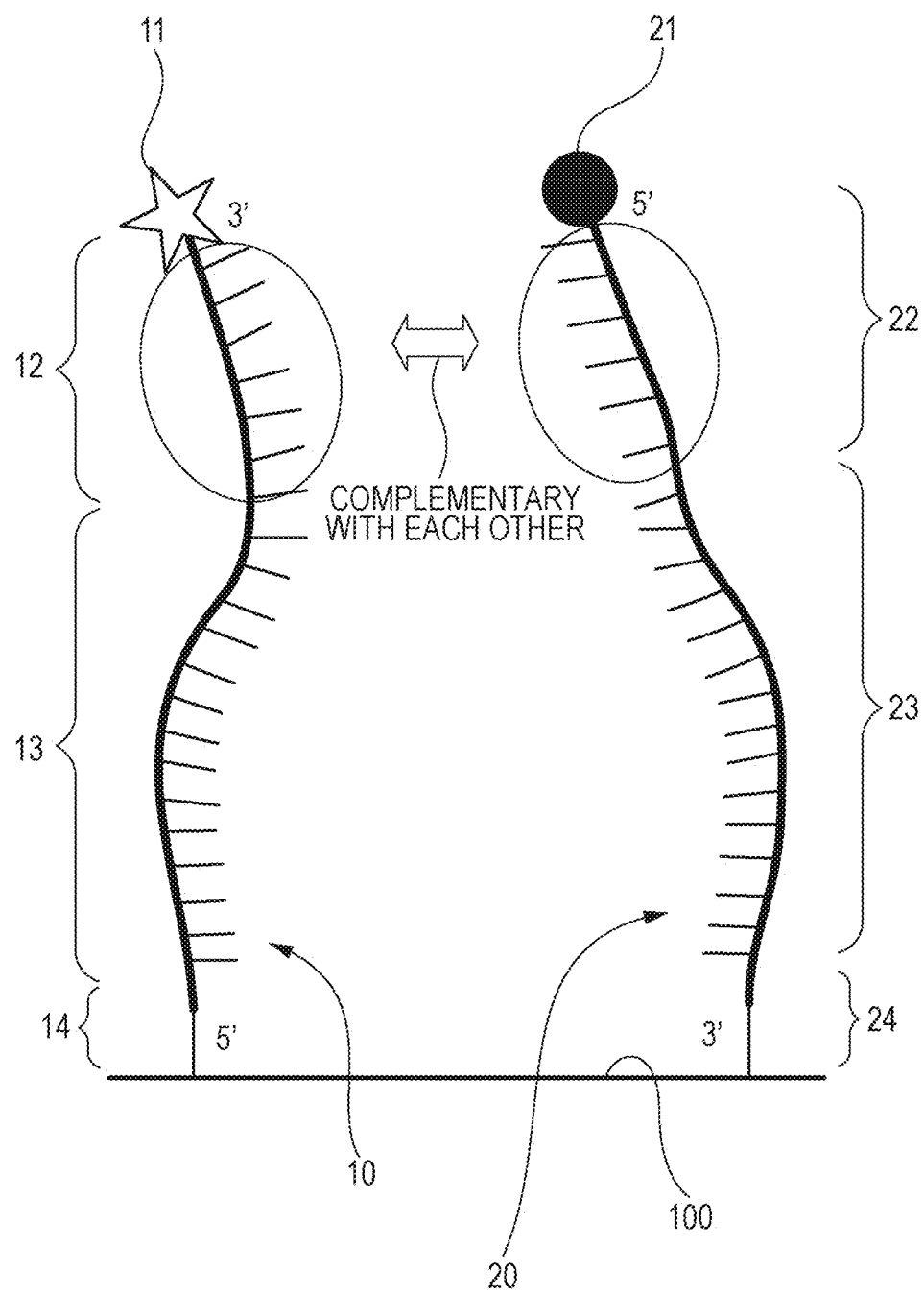
FIG. 2 is a diagram illustrating an exemplary structure of a probe provided on the nucleic acid sequence measuring device of FIG. 1.

FIG. 1 is a diagram illustrating an exemplary structure of a nucleic acid sequence measuring device used in the nucleic acid sequence measuring method according to this embodiment, and FIG. 2 is a diagram illustrating an exemplary structure of a probe used therein.

As illustrated in FIG. 1 and FIG. 2, the nucleic acid sequence measuring device (hereinafter also referred to as a DNA chip) includes a solid surface 100 of a substrate or the like, and a fluorescent probe 10 and a quenching probe 20 that are fixed to the solid surface 100. The fluorescent probe 10 includes a sequence complementary with a target 30, which is the nucleic acid to be detected, and a fluorescent molecule 11 added to the sequence. The quenching probe 20 includes a sequence complementary with the target 30, which is the nucleic acid to be detected, and a quenching substance 21 added to the sequence. This embodiment employs the principle of quenching by the fluorescence resonance energy transfer. Known substances applicable as a quenching substance 21 include DABCYL and BHQ.

As illustrated in FIG. 2, the fluorescent probe 10 includes the following in the order from the 3' end: a coupling part (X part) 12 including several bases, which is the sequence complementary with the target 30; a detection sequence 13, which is connected to the coupling part 12 and is the sequence complementary with the target 30; and a linker 14 that is connected to the detection sequence 13 and is coupled with the solid surface 100 at the 5' end. The fluorescent molecule 11 is fixed at the 3' end of the fluorescent probe 10.

The quenching probe 20 includes the following in the order from the 5' end: a coupling part (Y part) 22 including several bases; a detection sequence 23, which is connected to the coupling part 22 and is the sequence complementary with the target 30; and a linker 24 that is connected to the detection sequence 23 and is coupled with the solid surface 100 at the 3' end. The quenching substance 21 is fixed at the 5' end of the quenching probe 20.

The fluorescent probe 10 and the quenching probe 20 have their base ends fixed to the solid surface 100 through the linker 14 and the linker 24, respectively. Moreover, the nucleic acid sequence of the coupling part 12 of the fluorescent probe 10 and the nucleic acid sequence of the coupling part 22 of the quenching probe 20 are complementary with each other. The base ends of the fluorescent probe 10 and the quenching probe 20 are fixed to the solid surface 100 to have the positional relationship satisfying the following two conditions: the coupling part 12 of the fluorescent probe 10 and the coupling part 22 of the quenching probe 20 are able to couple with each other with their base ends fixed to the solid surface 100; and when the coupling part 12 of the fluorescent probe 10 and the coupling part 22 of the quenching probe 20 are coupled with each other, the quenching substance 21 approaches the fluorescent molecule 11 to make the fluorescent molecule 11 in the quenched state.

The affinity between the fluorescent probe 10 and the target 30 can be designed to be higher than the affinity between the fluorescent probe 10 and the quenching probe 20 that depends on the coupling part 12 and the coupling part 22.

Figure 3:
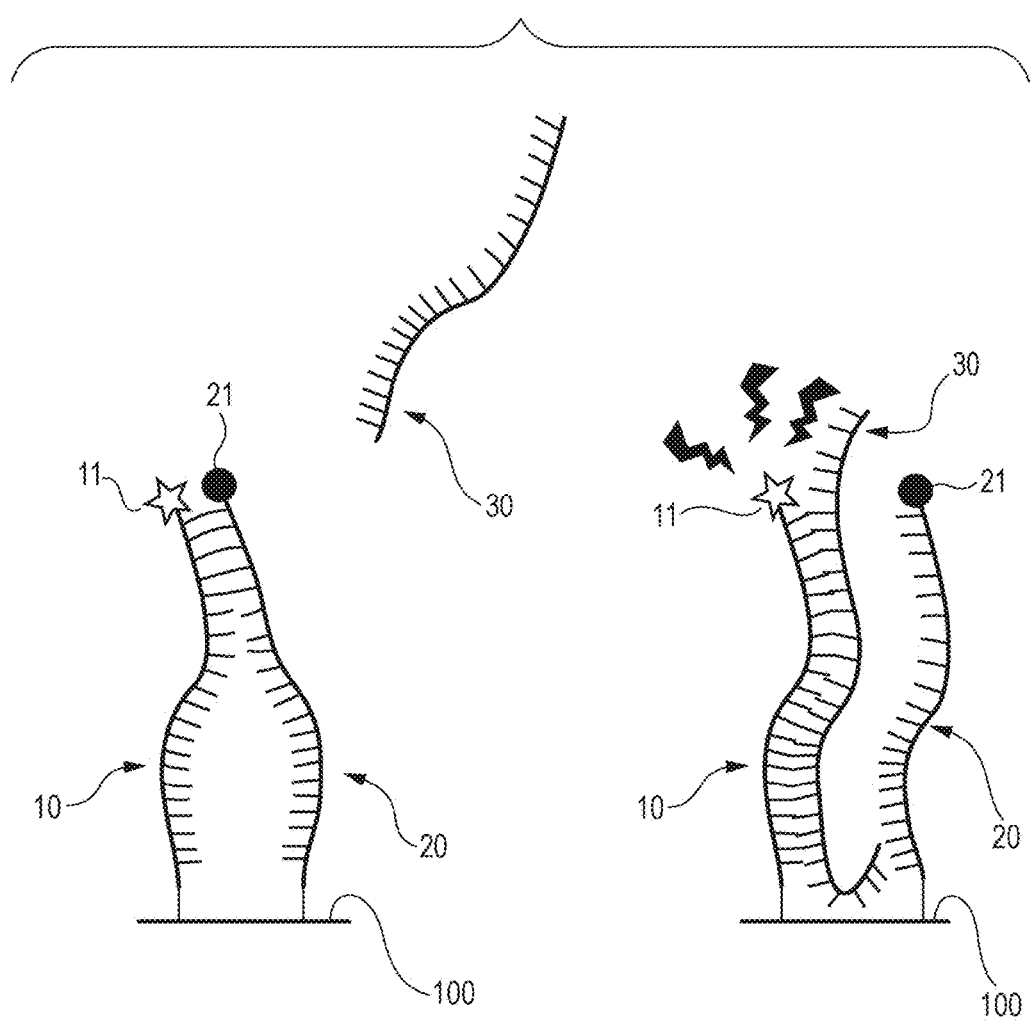
FIG. 3 is a schematic diagram illustrating the principle for detecting a target to be hybridized with the probe using the nucleic acid sequence measuring device of FIG. 1.

Next, description is made of the principle and the operating procedures for detecting the target 30 with the use of the DNA chip. FIG. 3 is a diagram schematically illustrating the principle of detecting the target and FIG. 4 is a diagram illustrating the operating procedures for detecting the target.

As illustrated in the left part of FIG. 3, the coupling parts 12 and the coupling parts 22 including several bases of the fluorescent molecule 11 and the quenching substance 21, which are adjacent to each other (FIG. 2), are coupled with each other in the absence of the target 30. This causes the fluorescent molecule 11 and the quenching substance 21 to get close to each other. In this state, the irradiation of the fluorescent molecule with the excitation light would not cause the fluorescent molecule 11 to emit the fluorescence due to the influence of the quenching substance 21.

Figure 4:
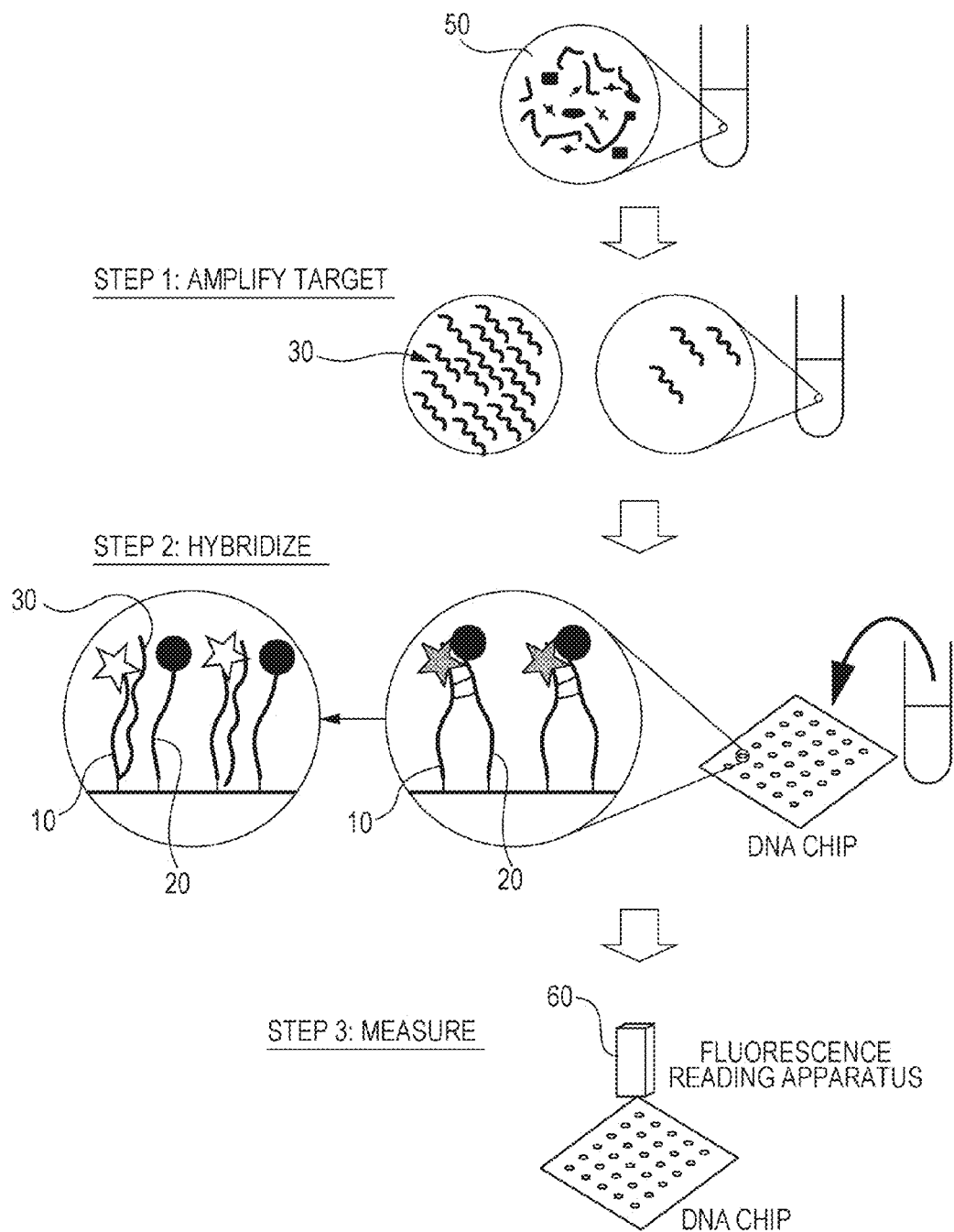
FIG. 4 a diagram illustrating the operating procedures for detecting the target.

Here, as illustrated in FIG. 4, a sample solution containing a sample 50 is prepared using a method known to a person skilled in the art, and then the gene (target 30) in the sample 50 is amplified (Step 1). Next, the target 30 and the fluorescent probe 10 are hybridized by supplying the sample solution containing the amplified target 30 to the solid surface 100 of the DNA chip (Step 2).

As illustrated in the right part of FIG. 3, in Step 2, the target 30 and the fluorescent probe 10 are coupled with each other to uncouple between the coupling part 12 and the coupling part 22. This increases the distance between the quenching substance 21 and the fluorescent molecule 11, thereby cancelling the quenched state. Thus, the irradiation of the fluorescent molecule 11 with the excitation light causes the fluorescent molecule 11 to emit the fluorescence. Thus, as illustrated in FIG. 4, from the observation of the solid surface 100 with the use of a fluorescence reading apparatus 60, it is possible to check the presence or absence of the target nucleic acid (target 30) in the sample by checking whether the fluorescent probe 10 emits the fluorescence or not (Step 3). On this occasion, the fluorescence is not emitted from the target 30 that is in the sample solution and not coupled with the fluorescent probe 10. Therefore, it is not necessary to wash away the target 30 that is not captured by this fluorescent probe 10. As a result, the solid surface 100 can be observed through this solution in the presence of the sample solution containing the target. Thus, the fluorescence intensity without the influence from the washing can be measured. Moreover, the real-time measurement can be performed during the hybridization.

In the stage (Step 1) of the amplification of the gene, a test of confirming the amplification of the gene may be conducted. The hybridization (Step 2) may be conducted only if the gene is amplified. Thus, the kind of gene (for example, the bacterial species thereof) can be examined by the operation of Step 2 and Step 3 just in the case where the sample 50 includes the gene. This can eliminate unnecessary costs for the DNA chip or measurement operation.

The timing of checking the presence or absence of the gene is not limited to the time after the amplification. The presence or absence of the gene may be checked during the amplification reaction. The method of checking includes electrophoresis, antigen-antibody reaction, mass spectrometry, and the real-time PCR method.

The nucleic acid (target 30) may be coupled with protein or sugar chain. In this case, the mutual operation of the protein or sugar chain relative to the nucleic acid (target 30) can be observed.

In this manner, according to the nucleic acid sequence measuring method of this embodiment, the probes fixed to the solid surface 100 are subjected to the fluorescence/quenching devise. Therefore, the molecule to be detected (target 30) can be detected in a state that the target 30 is not provided with anything including the fluorescent molecule. Therefore, the hybridization detection using the array (DNA chips) can be applied also to the system including the target molecules for which the modification with such as fluorescence is difficult. Further, the target molecule (target 30) does not emit the fluorescence by itself; therefore, the measurement is possible in the presence of the excess target molecule that is not captured by the probe. Thus, the step of washing the DNA chip before the detection can be omitted.

According to the nucleic acid sequence measuring method of this embodiment, the labeling step is unnecessary and moreover the washing step can be omitted; therefore, the time and effort required in the experiment of hybridization are further reduced. Thus, the working time and cost can be reduced. In addition, the nucleic acid sequence measuring method of the present embodiment can avoid any risk due to the absence of washing step, such as a decrease in performance, a decrease in fluorescence intensity, an increase in background fluorescence, or occurrence of variations. On the other hand, the known method has a risk of signal generation due to the way of washing, the degree of washing, uneven washing, or the like or a risk of increases in background fluorescence and variations thereof. In other words, the nucleic acid sequence measuring method of this embodiment can avoid such a kind of risk. Thus, the more uniform results can be obtained on the array surface, thereby improving the repeatability of the detection.

According to the nucleic acid sequence measuring method of this embodiment, the measured fluorescence intensity, i.e., the background fluorescence in the absence of the target can be reduced largely as compared to the DNA chip using the molecular beacon as the detection probe.

Figure 5:
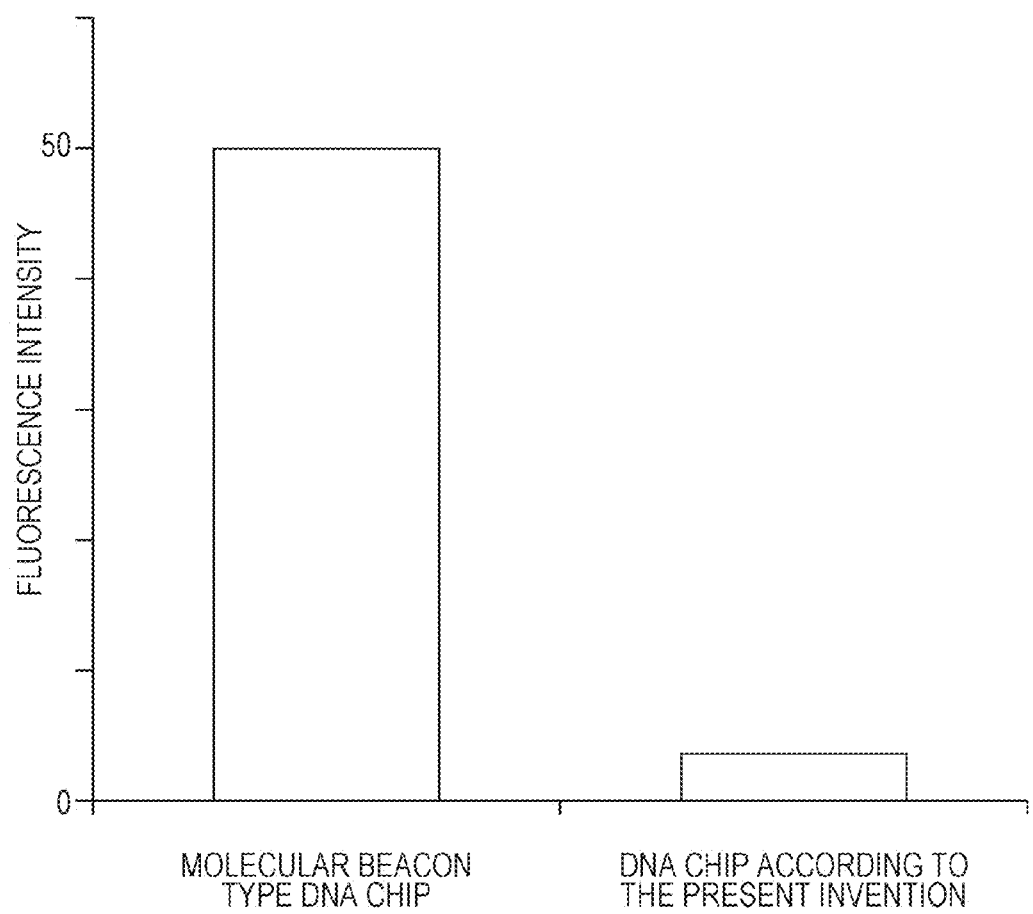
FIG. 5 is a graph representing the comparison between the DNA chip using the molecular beacon as the detection probe and the nucleic acid sequence measuring device used in the nucleic acid sequence measuring method according to an embodiment of the present disclosure with respect to spot fluorescence intensity in the absence of the target.

FIG. 5 is a graph illustrating the comparison between the DNA chip using the molecular beacon as the detection probe and the DNA chip used in the nucleic acid sequence measuring method of this embodiment with respect to spot fluorescence intensity in the absence of the target. As illustrated in FIG. 5, the experiments by the present inventors have proved that in the DNA chip used in the nucleic acid sequence measuring method of this embodiment, the spot fluorescence intensity in the absence of the target can be suppressed to be 1/10 or less as compared to the molecular beacon type DNA chip. This leads to the following estimation. That is, in the DNA chip according to this embodiment, the fluorescent probe and the quenching probe are formed as the independent probes. Therefore, the probes near the quenching substance and the fluorescent molecule easily form the stem structure in the absence of the target. According to this embodiment, the detection sensitivity or the measurement accuracy can be increased by the decrease in background fluorescence.

According to the nucleic acid sequence measuring method of this embodiment, the hybridization can be observed in real time. In other words, the array observation in the state (wet state) that the solution containing the detection target molecule (target) remains added to the DNA array is possible. This enables the checking of the fluorescence intensity without the influence of washing and the real-time observation of the hybridization. Therefore, the hybridization can be ended in a shorter time depending on the circumstances such as when the hybridization progresses rapidly because of high sample concentration.

Figure 6:
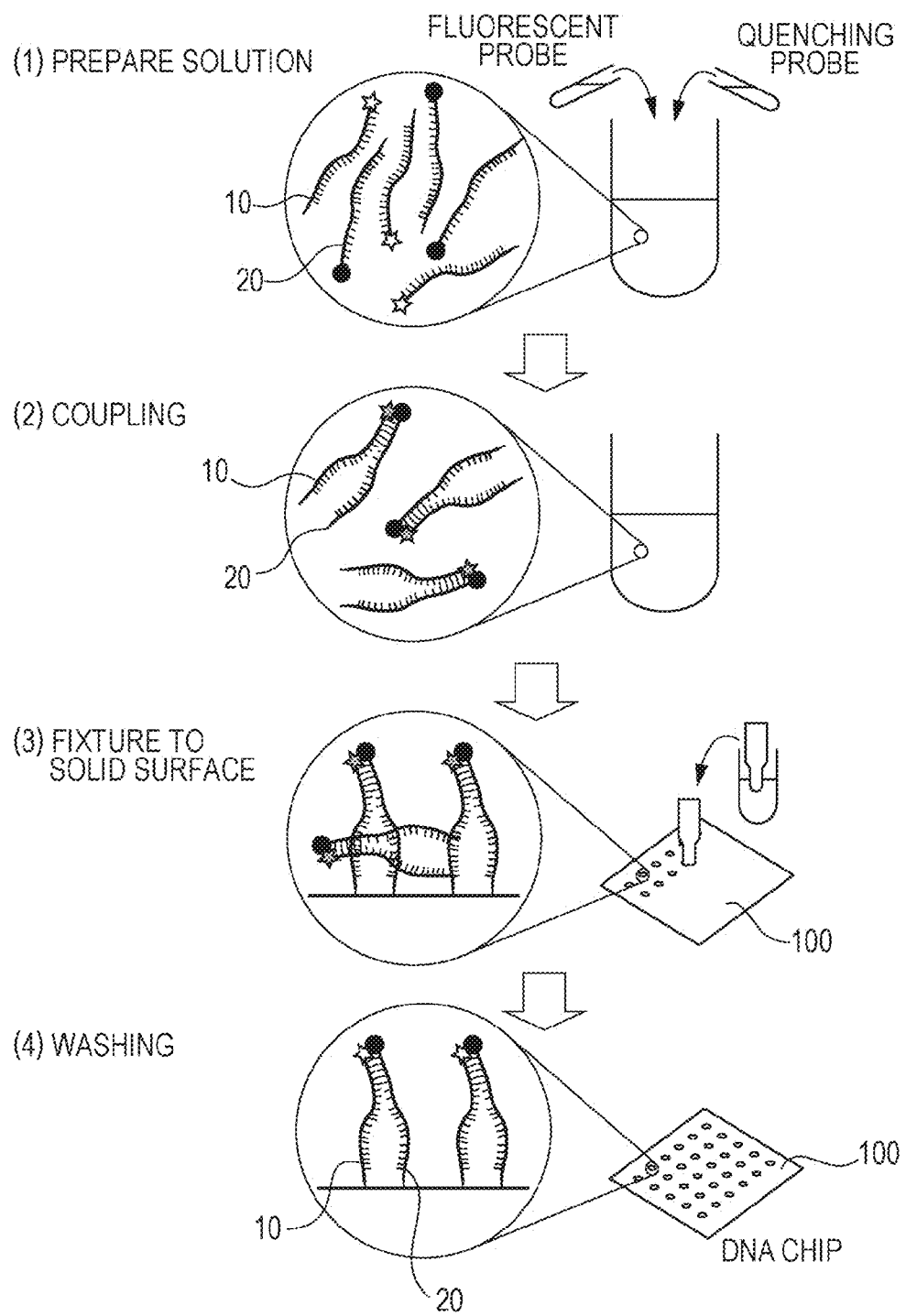
FIG. 6 is a diagram illustrating a manufacturing method for a nucleic acid sequence measuring device according to an embodiment of the present disclosure.

Next, description is made of a manufacturing method for the DNA chip according to the nucleic acid sequence measuring method of this embodiment. FIG. 6 is a diagram illustrating a manufacturing method for the DNA chip according to the nucleic acid sequence measuring method of this embodiment. Hereinafter procedures for manufacturing the DNA chip will be described with reference to FIG. 6.

(1) Preparation of Solution

First, a probe liquid is prepared by mixing the fluorescent probe 10 and the quenching probe 20, and then the concentration of the probe liquid is adjusted.

(2) Coupling

Next, the probe liquid is heated and then cooled rapidly to couple the fluorescent probe 10 and the quenching probe 20 with each other. In other words, the fluorescent probe 10 and the quenching probe 20 are coupled with each other through the coupling part 12 and the coupling part 22. Here, for example, the probe liquid is heated at 95° C. and the temperature is maintained for five minutes, and then the liquid is cooled rapidly to 25° C.; thus, the fluorescent probe 10 and the quenching probe 20 are coupled with each other.

(3) Fixture to Solid Surface

Next, the probe liquid including the fluorescent probe 10 and the quenching probe 20 in the coupled state is added to the solid surface, thereby fixing the fluorescent probe 10 and the quenching probe 20 to the solid surface 100.

(4) Washing

Next, the solid surface 100 is washed, thereby removing the excess probe that is not fixed. The DNA chip is manufactured through the above procedures.

In the state that the fluorescent probe 10 and the quenching probe 20 are coupled with each other through the coupling part 12 and the coupling part 22, the fluorescent probe 10 and the quenching probe 20 have their base ends coupled to the solid surface 100. Thus, the positional relationship between the fluorescent probe 10 and the quenching probe 20 can be managed as appropriate and the quenching effect can be exhibited as appropriate. Therefore, the detection sensitivity can be improved.

The nucleic acid sequence measuring method according to the present disclosure can be variously modified as below without being limited to the above embodiment.

The quenching efficiency in the quenched state can be controlled by fixing the base ends to the solid surface while changing the presence ratio between the fluorescent probe modified with the fluorescent molecule and the quenching probe modified with the quenching substance. For example, when the number of quenching probes is larger than the number of fluorescent probes, the probability of coupling the fluorescent probes with the quenching substances is increased. This increases the quenching efficiency in the quenched state. Thus, the fluorescence (offset fluorescence intensity) in the absence of the target molecule can be suppressed. When the number of fluorescent probes is larger than the number of quenching probes, the probability of having the fluorescent probes subjected to the quenching operation is decreased; thus, the fluorescence quantity (fluorescence intensity of the hybridization) exhibited by the fluorescent probe after the detection of the target substance becomes larger.

Figure 7:
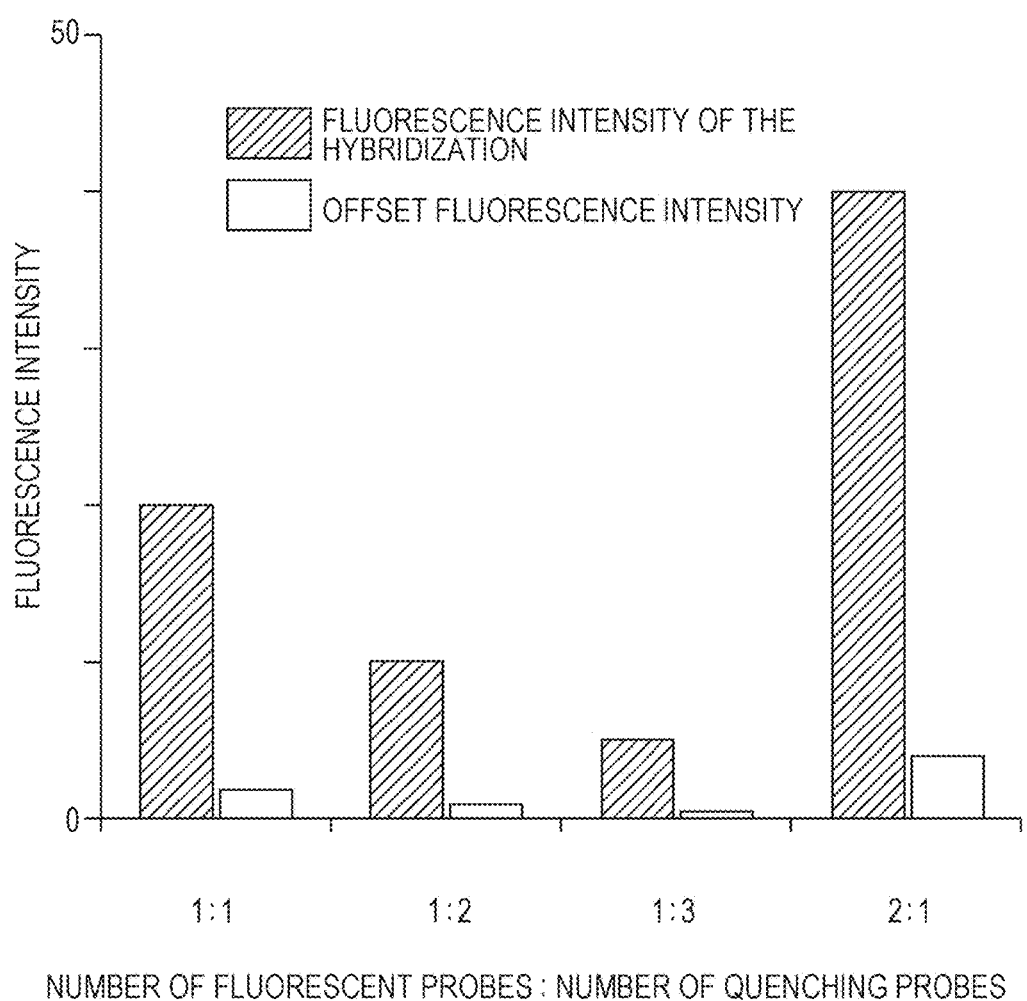
FIG. 7 is a graph representing the change of the fluorescence intensity of the hybridization and the offset fluorescence intensity if the presence ratio between the fluorescent probe and the quenching probe is changed.

FIG. 7 is a graph illustrating the changes of the fluorescence intensity of the hybridization and the offset fluorescence intensity in the case where the presence ratio between the fluorescent probe and the quenching probe (ratio between the number of fluorescent probes and the number of quenching probe in the probe liquid) is changed. As indicated by FIG. 7, according to the experiments by the present inventors, the offset fluorescence intensity is decreased as the number of quenching probes is larger than the number of fluorescent probes (see the cases in which the number of fluorescent probes:the number of quenching probes=1:1, 1:2, 1:3). When the number of fluorescent probes is larger than the number of quenching probes, the fluorescence intensity of the hybridization is increased (see the case in which the number of fluorescent probes:the number of quenching probes=2:1).

Figure 8:
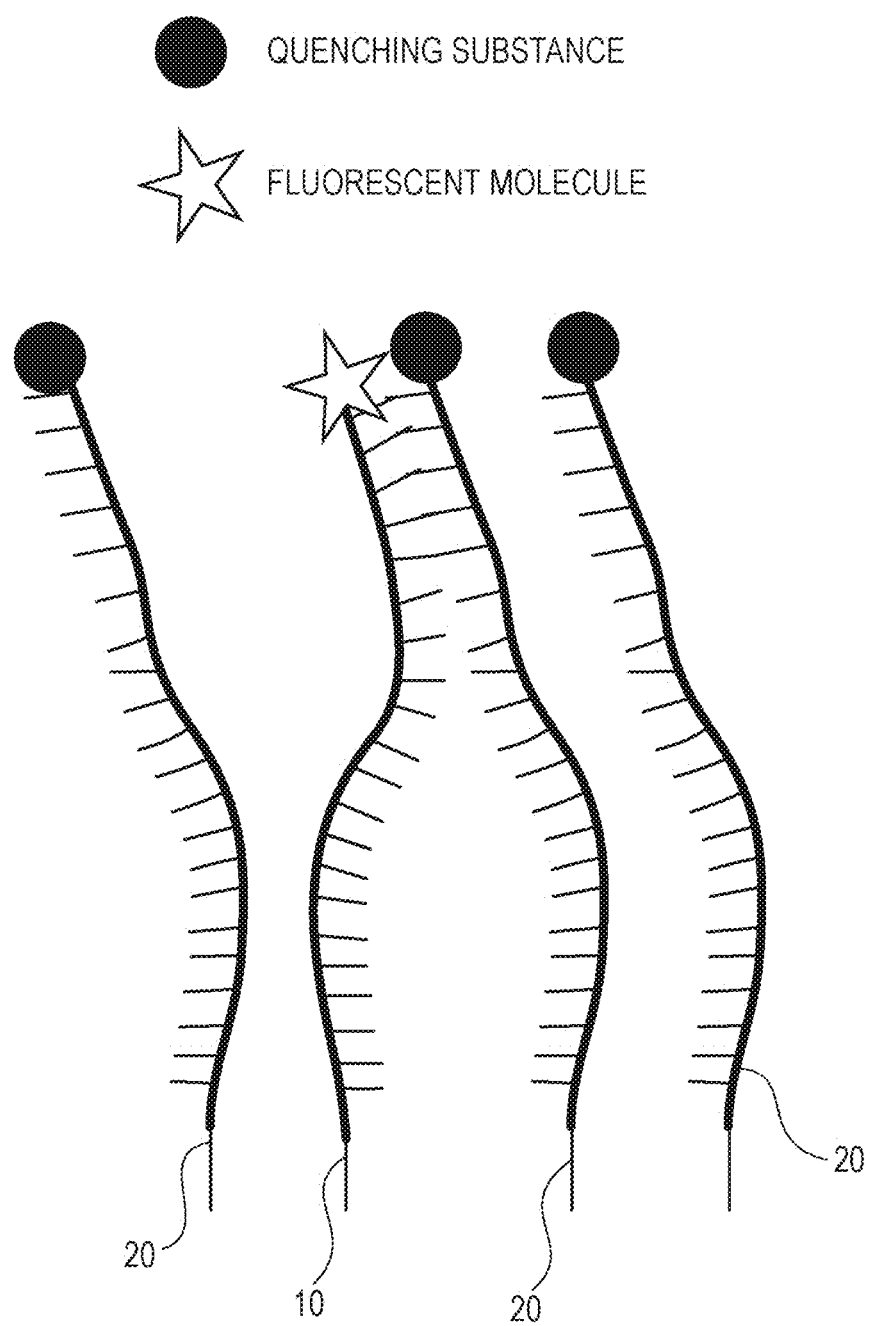
FIG. 8 is a schematic diagram illustrating the probe in the case where the number of quenching probes is larger than the number of fluorescent probes.

FIG. 8 is a schematic diagram illustrating the case in which the number of quenching probes is larger than the number of fluorescent probes. As illustrated in FIG. 8, when the number of quenching probes fixed onto the DNA chip is larger than the number of fluorescent probes, the fluorescent probe 10 not coupled with the quenching probe 20 is generated less frequently. It is estimated that this decreases the offset fluorescence intensity. In the example of FIG. 8, the offset fluorescence intensity is the lowest when the ratio between the number of fluorescent probes and the number of quenching probes is 1:3.

In the above embodiment, the sequence of the coupling part 12 of the fluorescent probe 10 is complementary with the target 30. However, the sequence of the coupling part 12 of the fluorescent probe 10 and the coupling part 22 of the quenching probe 20 may be a mutually complementary and constant sequence regardless of the kind of the target. In other words, the coupling part 12 and the coupling part 22 always have the same sequence independently of the kind of target and just the detection sequence 13 and the detection sequence 23 (FIG. 2) may be changed according to the kind of the target. In this case, therefore, the following advantages are given: the probes are easily designed; and the quenching/light-emitting characteristics are constant regardless of the detection target.

Figure 9A:
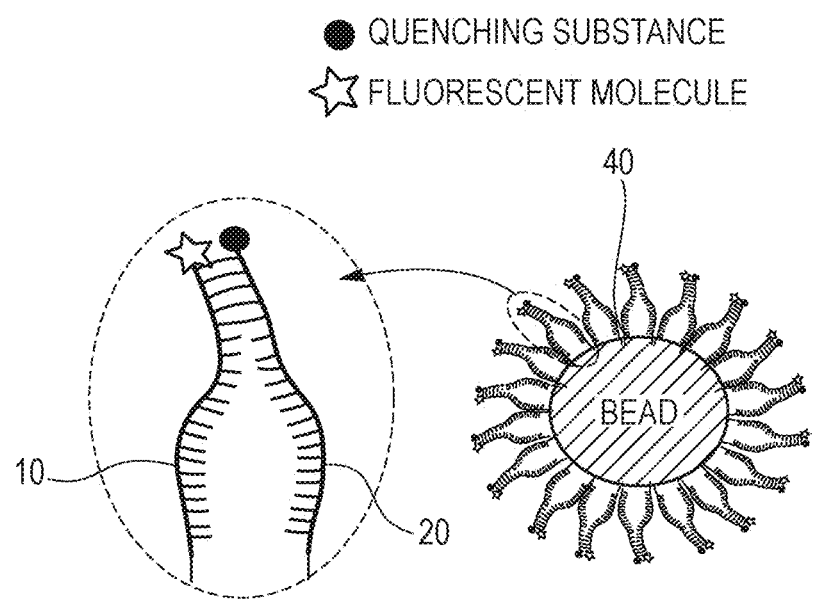
FIG. 9A is a diagram illustrating a modified example of a nucleic acid sequence measuring device according to an embodiment of the present disclosure, in which a surface of a bead is used as the solid surface.

The solid surface to which the fluorescent probe and the quenching probe are fixed is not limited to the flat plane on the substrate. For example, the solid surface may be a surface (spherical surface) of a sphere (hereinafter also referred to as a bead). That is, the fluorescent probe and the quenching probe may be fixed to the bead surface. FIG. 9A illustrates an example in which the fluorescent probe and the quenching probe are fixed to the bead surface. As illustrated in FIG. 9A, the base ends of the fluorescent probe 10 and the quenching probe 20 are fixed to the surface of a bead 40. This causes the fluorescent probe 10 and the quenching probe 20 to have a shape expanding radially around the bead 40. In this case, the solid surface on which the base end of the probe is fixed has a larger surface area, thereby increasing the amount of probes per unit area. Moreover, by collecting the beads that have captured the detection target molecules in accordance with the size, magnetism, or the like, the detection target molecule can be collected as selected. The collected molecules can be used in, for example, another test of a later step.

Figure 9B:
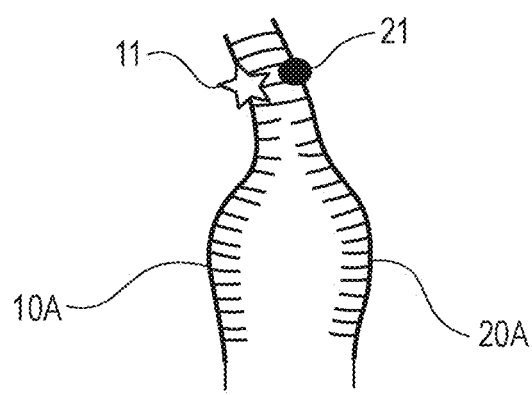
FIG. 9B is a diagram illustrating a modified example of a nucleic acid sequence measuring device according to an embodiment of the present disclosure, in which the fluorescent molecule and the quenching substance are each located in the middle of the probe.

The fluorescent molecule or the quenching substance may not adhere to the end of the probe. For example, in the example of FIG. 9B, the fluorescent molecule 11 and the quenching substance 21 are added to the middle of a fluorescent probe 10A and a quenching probe 20A, respectively. In this case, the probe can be designed so that the quenching substance 21 and the fluorescent molecule 11 face each other closely in the state that the fluorescent probe 10A and the quenching probe 20A are coupled with each other so that the quenching operation is produced. In the case of adding the fluorescent molecule or the quenching substance to the position other than the end of the probe, the end of the probe can be modified differently, which is advantageous.

Figure 10A:
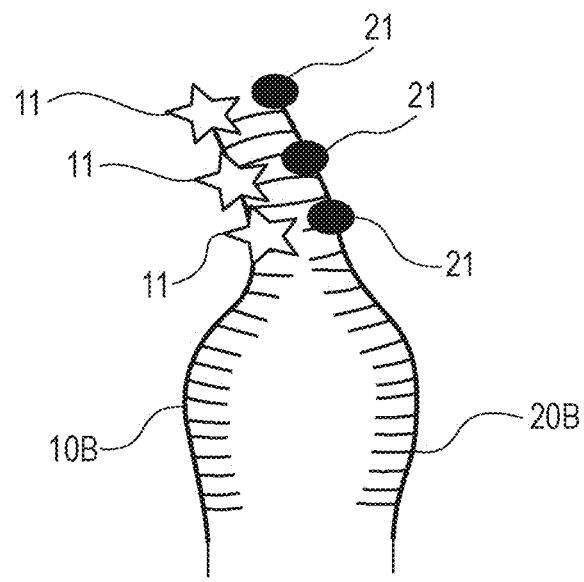
FIG. 10A is a diagram illustrating a modified example of a nucleic acid sequence measuring device according to an embodiment of the present disclosure, in which the fluorescent molecules and the quenching substances are added at a plurality of positions of the probes.

A plurality of kinds of fluorescent molecules and quenching substances may be added to a plurality of positions in the fluorescent probe and the quenching probe. FIG. 10A is a diagram illustrating an example in which the fluorescent molecules and the quenching substances are added at a plurality of positions. In the example of FIG. 10A, the fluorescent molecules 11, 11, and 11 are added to the fluorescent probe 10B and the quenching substances 21, 21, and 21 are added to the quenching probe 20B. In the case of adding the plurality of fluorescent molecules and quenching substances to each probe, the kinds of fluorescent molecules and quenching substances may vary. In the case where the plurality of fluorescent molecules and quenching substances is added to each probe, the fluorescence quantity when the detection target molecules are coupled increases, thereby enabling more sensitive detection.

In the above embodiment, in addition to that the fluorescent probe 10 has the detection sequence 13, the quenching probe 20 has the detection sequence 23. Alternatively, just the fluorescent probe may have the detection sequence complementary with the target. However, when the both probes have the detection sequence, the coupling frequency of the target can be increased.

In the above embodiment, the target 30 is designed to be coupled with the fluorescent probe 10. However, the probe may be designed so that the target is coupled with the quenching probe 20. In this case, the change in characteristic of the fluorescent molecule due to the proximity of the target can be avoided.

Figure 10B:
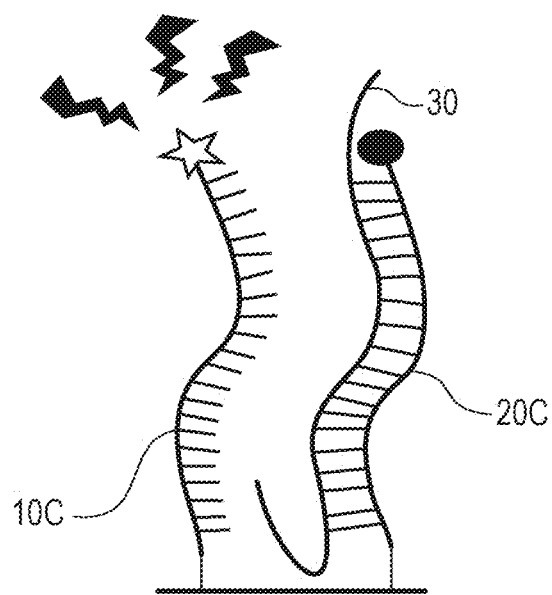
FIG. 10B is a diagram illustrating a modified example of a nucleic acid sequence measuring device according to an embodiment of the present disclosure, in which the target is coupled with the quenching probe.

FIG. 10B is a diagram illustrating an example in which the target is coupled with the quenching probe. As illustrated in FIG. 10B, the target 30 may be coupled with a quenching probe 20C instead of with a fluorescent probe 10C when the quenching probe 20C has the sequence with higher affinity to the target 30 than the sequence of the fluorescent probe 10C. In this case, the fluorescent probe 10C may or may not have the detection sequence complementary with the target.

Figure 11A:
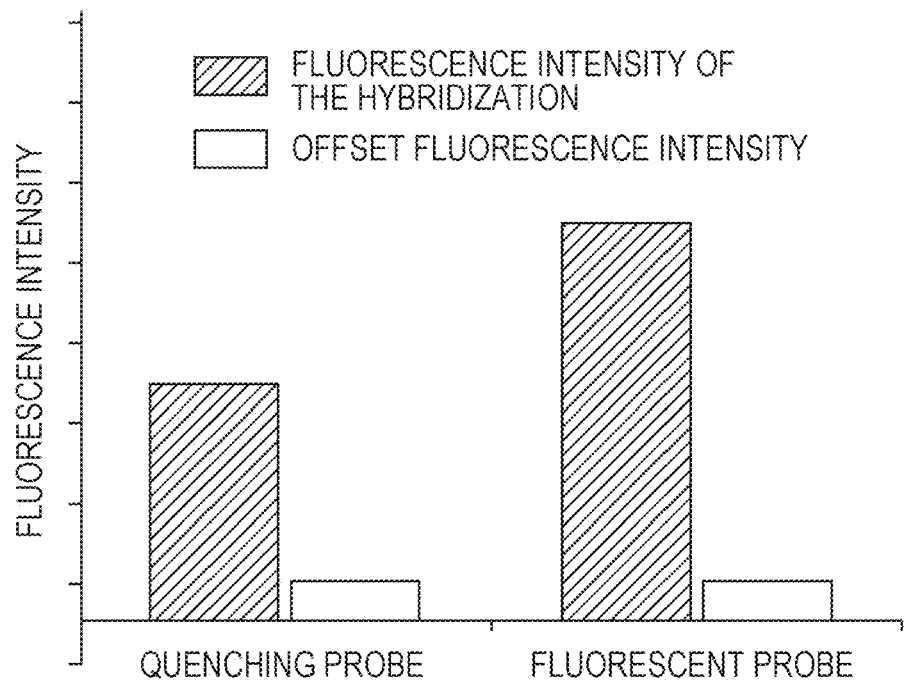
FIG. 11A is a graph representing the comparison results between the fluorescence intensity of the hybridization and the offset fluorescence intensity for each of the case where the target is coupled with the fluorescent probe and the case where the target is coupled with the quenching probe.
Figure 11B:
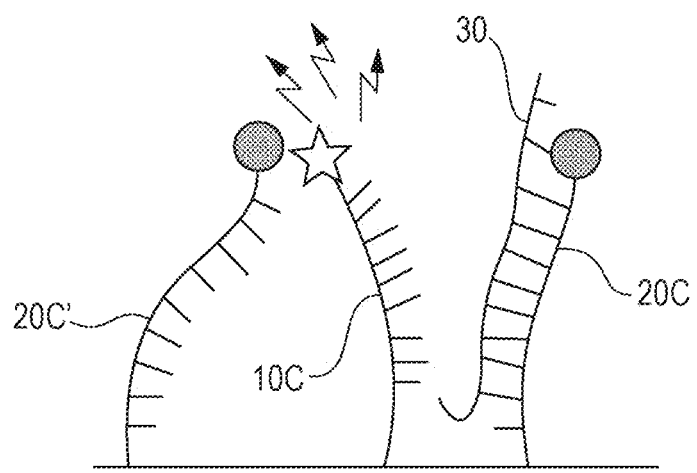
FIG. 11B is a diagram illustrating the state of quenching by the quenching probe that is not coupled with the target and that is adjacent to the fluorescent probe.

According to the experiments by the present inventors, when the target is coupled with the fluorescent probe, the offset fluorescence intensity remains the same but the fluorescence intensity of the hybridization is higher as compared to when the target is coupled with the quenching probe. FIG. 11A is a graph illustrating the comparison results between the fluorescence intensity of the hybridization and the offset fluorescence intensity for each of the case where the target is coupled with the fluorescent probe and the case where the target is coupled with the quenching probe. The fluorescence intensity of the hybridization is suppressed when the target is coupled with the quenching probe. It is estimated from the above that the quenching effect is obtained by the quenching probe that is adjacent to the fluorescent probe and that is not coupled with the target. FIG. 11B illustrates the state in which the effect as above is produced. As illustrated in FIG. 11B, the fluorescence from the fluorescent probe 10C is quenched by a quenching probe 20C' that is not coupled with the target 30 and is adjacent to the fluorescent probe 10C when the target 30 is coupled with the quenching probe 20C.

The application range of the present invention is not limited to the above embodiment. The present disclosure can be widely applied to, for example, a nucleic acid sequence measuring method using a nucleic acid sequence measuring device for measuring a target having a predetermined nucleic acid sequence in a sample through the hybridization between the target and the probe.

The nucleic acid sequence measuring method according to the present disclosure may be related to any of the following first and second nucleic acid sequence measuring methods, first to fifth nucleic acid sequence measuring devices, first manufacturing method for the nucleic acid sequence measuring device, and first and second nucleic acid sequence measuring apparatus.

A first nucleic acid sequence measuring method is a nucleic acid sequence measuring method using a nucleic acid sequence measuring device that measures a target having a predetermined nucleic acid sequence in a sample by hybridization, the nucleic acid sequence measuring device including a fluorescent probe and a quenching probe that are independent from each other and a solid surface to which a base end of the fluorescent probe and a base end of the quenching probe are fixed, wherein: a fluorescent molecule is added to the fluorescent probe and a quenching substance is added to the quenching probe; the fluorescent probe or the quenching probe has a coupling part with a complementary sequence; the fluorescent probe or the quenching probe is provided with a detection part with a sequence complementary with the nucleic acid sequence; and when the target is not supplied, coupling through the coupling parts is maintained to quench fluorescence of the fluorescent molecule due to the quenching substance that has approached the fluorescent molecule, and when the target is supplied, the coupling through the coupling parts is canceled because the target is coupled with the detection part, thereby causing the fluorescent molecule to emit fluorescence due to separation of the quenching substance from the fluorescent molecule, the nucleic acid sequence measuring method including: a step of hybridization with the use of the nucleic acid sequence measuring device; and a step of measuring fluorescence from the nucleic acid sequence measuring device for which hybridization has been conducted.

A second nucleic acid sequence measuring method is the first nucleic acid sequence measuring method wherein, in the step of measuring the fluorescence, the fluorescence from the nucleic acid sequence measuring device is measured in a state that a solution supplied to the nucleic acid sequence measuring device is not washed.

A first nucleic acid sequence measuring device is a nucleic acid sequence measuring device measuring a target having a predetermined nucleic acid sequence in a sample by hybridization, and includes a fluorescent probe and a quenching probe that are independent from each other, and a solid surface to which a base end of the fluorescent probe and a base end of the quenching probe are fixed, wherein: a fluorescent molecule is added to the fluorescent probe and a quenching substance is added to the quenching probe; the fluorescent probe or the quenching probe has a coupling part with a complementary sequence; the fluorescent probe or the quenching probe is provided with a detection part with a sequence complementary with the nucleic acid sequence; and when the target is not supplied, coupling through the coupling parts is maintained to quench fluorescence of the fluorescent molecule due to the quenching substance that has approached the fluorescent molecule, and when the target is supplied, the coupling through the coupling parts is canceled because the target is coupled with the detection part, thereby causing the fluorescent molecule to emit fluorescence due to separation of the quenching substance from the fluorescent molecule.

A second nucleic acid sequence measuring device is the first nucleic acid sequence measuring device, wherein the fluorescent probe has the detection part.

A third nucleic acid sequence measuring device is the first or second nucleic acid sequence measuring device, wherein the solid surface is provided on a flat substrate or a bead.

A fourth nucleic acid sequence measuring device is any of the first to third nucleic acid sequence measuring devices, wherein at least a part of the coupling part functions as the detection part.

A fifth nucleic acid sequence measuring device is any of the first to fourth nucleic acid sequence measuring devices, wherein the number of quenching probes is larger than that of fluorescent probes.

A first manufacturing method for a nucleic acid sequence measuring device is a manufacturing method for a nucleic acid sequence measuring device that measures a target having a predetermined nucleic acid sequence in a sample by hybridization, the nucleic acid sequence measuring device including a fluorescent probe and a quenching probe that are independent from each other, and a solid surface to which a base end of the fluorescent probe and a base end of the quenching probe are fixed, wherein: a fluorescent molecule is added to the fluorescent probe and a quenching substance is added to the quenching probe; the fluorescent probe or the quenching probe has a coupling part with a complementary sequence; the fluorescent probe or the quenching probe is provided with a detection part with a sequence complementary with the nucleic acid sequence; and when the target is not supplied, coupling through the coupling parts is maintained to quench fluorescence of the fluorescent molecule due to the quenching substance that has approached the fluorescent molecule, and when the target is supplied, the coupling through the coupling parts is canceled because the target is coupled with the detection part, thereby causing the fluorescent molecule to emit fluorescence due to separation of the quenching substance from the fluorescent molecule, the manufacturing method for the nucleic acid sequence measuring device including: a step of coupling the fluorescent probe and the quenching probe through the coupling parts; and a step of coupling the fluorescent probe and the quenching probe to the solid surface with the probes coupled with each other through the coupling parts.

A first nucleic acid sequence measuring apparatus is a nucleic acid sequence measuring apparatus that measures, with the use of a nucleic acid sequence measuring device, a target having a predetermined nucleic acid sequence in a sample by hybridization, the nucleic acid sequence measuring device including a fluorescent probe and a quenching probe that are independent from each other, and a solid surface to which a base end of the fluorescent probe and a base end of the quenching probe are fixed, wherein: a fluorescent molecule is added to the fluorescent probe and a quenching substance is added to the quenching probe; the fluorescent probe or the quenching probe has a coupling part with a complementary sequence; the fluorescent probe or the quenching probe is provided with a detection part with a sequence complementary with the nucleic acid sequence; when the target is not supplied, coupling through the coupling parts is maintained to quench fluorescence of the fluorescent molecule due to the quenching substance that has approached the fluorescent molecule, and when the target is supplied, the coupling through the coupling parts is canceled because the target is coupled with the detection part, thereby causing the fluorescent molecule to emit fluorescence due to separation of the quenching substance from the fluorescent molecule; and the nucleic acid sequence measuring apparatus measures the fluorescence from the nucleic acid sequence measuring device for which hybridization has been conducted.

A second nucleic acid sequence measuring apparatus is the first nucleic acid sequence measuring apparatus wherein the nucleic acid sequence measuring apparatus measures the fluorescence from the nucleic acid sequence measuring device in a state that a solution supplied to the nucleic acid sequence measuring device is not washed.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A nucleic acid sequence measuring method comprising:
   preparing a sample solution containing a target nucleic acid;
   supplying the sample solution to a nucleic acid sequence measuring device; and
   measuring fluorescence from the nucleic acid sequence measuring device, the nucleic acid sequence measuring device including:
   a fluorescent probe having a coupling part and a base end and added with a fluorescent molecule at a predetermined position;
   a quenching probe having a coupling part and a base end and added with a quenching substance at a predetermined position; and
   a substrate having a solid surface to which the base end of each of the fluorescent probe and the quenching probe is fixed, wherein:

the coupling part of the fluorescent probe and the coupling part of the quenching probe each have a mutually complementary nucleic acid sequence;

at least one of the fluorescent probe and the quenching probe has a detection part with a nucleic acid sequence complementary with a particular nucleic acid sequence; and the base end of the fluorescent probe and the base end of the quenching probe are fixed to the solid surface, the probes are in such a positional relationship that fluorescence from the fluorescent molecule is quenched by the quenching substance that has approached the fluorescent molecule by maintaining the coupling between the fluorescent probe and the quenching probe through the coupling parts when the hybridization between the target nucleic acid and the detection part has not occurred, and that fluorescence is emitted from the fluorescent molecule separated from the quenching substance due to canceling of the coupling between the fluorescent probe and the quenching probe through the coupling parts when the hybridization between the target nucleic acid and the detection part has occurred.

2. The nucleic acid sequence measuring method according to claim 1, wherein the fluorescence from the nucleic acid sequence measuring device is measured in the presence of the sample solution.

3. A nucleic acid sequence measuring device configured to measure a predetermined nucleic acid sequence of a target nucleic acid in a sample solution, comprising:

a fluorescent probe having a coupling part and a base end and added with a fluorescent molecule at a predetermined position;

a quenching probe having a coupling part and a base end and added with a quenching substance at a predetermined position; and a substrate having a solid surface to which the base end of each of the fluorescent probe and the quenching probe is fixed, wherein:

the coupling part of the fluorescent probe and the coupling part of the quenching probe each have a mutually complementary nucleic acid sequence;

at least one of the fluorescent probe and the quenching probe has a detection part with a nucleic acid sequence complementary with a particular nucleic acid sequence; and the base end of the fluorescent probe and the base end of the quenching probe are fixed to the solid surface, the probes are in such a positional relationship that fluorescence from the fluorescent molecule is quenched by the quenching substance that has approached the fluorescent molecule by maintaining the coupling between the fluorescent probe and the quenching probe through the coupling parts when the hybridization between the target nucleic acid and the detection part has not occurred, and that fluorescence is emitted from the fluorescent molecule separated from the quenching substance due to canceling of the coupling between the fluorescent probe and the quenching probe through the coupling parts when the hybridization between the target nucleic acid and the detection part has occurred.

4. The nucleic acid sequence measuring device according to claim 3, wherein the fluorescent probe has the detection part.

5. The nucleic acid sequence measuring device according to claim 3, wherein the substrate is a flat plate and the solid surface is one plane of the flat plate.

6. The nucleic acid sequence measuring device according to claim 3, wherein the substrate is a sphere and the solid surface is a spherical surface of the sphere.

7. The nucleic acid sequence measuring device according to claim 3, wherein at least a part of the coupling part functions as the detection part.

8. The nucleic acid sequence measuring device according to claim 3, wherein the number of quenching probes is larger than that of fluorescent probes.

9. The nucleic acid sequence measuring device according to claim 8, wherein the ratio between the number of fluorescent probes and the number of quenching probes is 1:3.

10. The nucleic acid sequence measuring device according to claim 3, wherein the predetermined position at which the fluorescent molecule and the quenching substance are added is in the middle of the fluorescent probe and the quenching probe.

11. The nucleic acid sequence measuring device according to claim 3, wherein there is a plurality of predetermined positions at which the fluorescent molecule and the quenching substance are added.

12. The nucleic acid sequence measuring device according to claim 3, wherein both the fluorescent probe and the quenching probe have the detection part.

13. A manufacturing method for the nucleic acid sequence measuring device according to claim 3, comprising:

coupling the fluorescent probe and the quenching probe through the coupling parts; and coupling the fluorescent probe and the quenching probe to the solid surface with the probes coupled with each other through the coupling parts.

14. A nucleic acid sequence measuring apparatus comprising:

the nucleic acid sequence measuring device according to claim 3; and a fluorescence reading apparatus configured to measure the fluorescence from the nucleic acid sequence measuring device.

15. The nucleic acid sequence measuring apparatus according to claim 14, wherein the fluorescence from the nucleic acid sequence measuring device is measured in the presence of the sample solution.

16. The nucleic acid sequence measuring device according to claim 3, wherein the fluorescent molecule is positioned distally from the base end of the fluorescent probe, and the quenching substance is positioned distally from the base end of the quenching probe.

* * * * *